(12) United States Patent
Lv et al.

(10) Patent No.: US 10,717,043 B2
(45) Date of Patent: Jul. 21, 2020

(54) MULTIFUNCTIONAL AIR PURIFYING DEVICE FOR REMOVING INDOOR POLLUTION BY THERMAL DECOMPOSITION

(71) Applicant: Dalian University of Technology, Dalian, Liaoning (CN)

(72) Inventors: Yang Lv, Liaoning (CN); Haifeng Wang, Liaoning (CN)

(73) Assignee: Dalian University of Technology, Dalian (CN)

( * ) Notice: Subject to any disclaimer, the term of this patent is extended or adjusted under 35 U.S.C. 154(b) by 219 days.

(21) Appl. No.: 16/079,536

(22) PCT Filed: Sep. 18, 2016

(86) PCT No.: PCT/CN2016/099195
§ 371 (c)(1),
(2) Date: Aug. 23, 2018

(87) PCT Pub. No.: WO2017/156993
PCT Pub. Date: Sep. 21, 2017

(65) Prior Publication Data
US 2019/0015780 A1 Jan. 17, 2019

(30) Foreign Application Priority Data
Mar. 15, 2016 (CN) .......................... 2016 1 0146711

(51) Int. Cl.
*B01D 53/75* (2006.01)
*A61L 9/14* (2006.01)
(Continued)

(52) U.S. Cl.
CPC .............. *B01D 53/75* (2013.01); *A61L 9/014* (2013.01); *A61L 9/20* (2013.01); *B01D 45/04* (2013.01); *B01D 46/0038* (2013.01); *B01D 53/04* (2013.01); *B01D 53/0407* (2013.01); *B01D 53/86* (2013.01); *B01D 53/869* (2013.01); *B01D 53/8668* (2013.01); *F24F 1/02* (2013.01); *F24F 3/14* (2013.01); *F24F 3/1603* (2013.01); *F24F 6/00* (2013.01); *F24F 13/28* (2013.01); *A61L 2209/12* (2013.01); *A61L 2209/14* (2013.01); *B01D 46/0023* (2013.01); *B01D 46/0036* (2013.01); *B01D 50/002* (2013.01); *B01D 2253/102* (2013.01); *B01D 2257/708* (2013.01);
(Continued)

(58) Field of Classification Search
CPC .............. B01D 53/75; A61L 9/14; A61L 9/20
USPC ........................................................ 422/121
See application file for complete search history.

(56) References Cited

U.S. PATENT DOCUMENTS

2011/0223071 A1* 9/2011 Kang ................. B01D 46/0036
422/169

* cited by examiner

Primary Examiner — Kevin Joyner

(57) ABSTRACT

A multifunctional air purifying device for removing indoor pollution by a thermal decomposition method comprises an air treatment unit and an air collection heater. The air collection heater is provided with an infrared lamp tube and an ultraviolet lamp tube. An annular water tank is arranged on an inner side of the upper part of the air treatment unit. A filter screen runs through the annular water tank and is connected with an air cap, and a fan is provided at a joint between the filter screen and the air cap. The filter screen includes an early effect filter screen, a HEPA filter screen, an activated carbon filter screen and a cold catalyst filter arranged in that order from a bottom to a top. A humidifier connects the annular sink and a nozzle located at an exhaust port.

4 Claims, 1 Drawing Sheet

(51) Int. Cl.
  *A61L 9/20* (2006.01)
  *F24F 13/28* (2006.01)
  *B01D 53/86* (2006.01)
  *F24F 3/14* (2006.01)
  *B01D 53/04* (2006.01)
  *F24F 1/02* (2019.01)
  *A61L 9/014* (2006.01)
  *B01D 45/04* (2006.01)
  *B01D 46/00* (2006.01)
  *F24F 3/16* (2006.01)
  *F24F 6/00* (2006.01)
  *B01D 50/00* (2006.01)

(52) U.S. Cl.
  CPC .. *B01D 2257/7027* (2013.01); *B01D 2257/90* (2013.01); *B01D 2259/4508* (2013.01); *F24F 2003/1628* (2013.01); *F24F 2003/1664* (2013.01); *F24F 2003/1667* (2013.01); *Y02A 50/22* (2018.01)

MULTIFUNCTIONAL AIR PURIFYING DEVICE FOR REMOVING INDOOR POLLUTION BY THERMAL DECOMPOSITION

BACKGROUND OF THE INVENTION

1. Field of the Invention

The present invention relates to air environment purifying technical field, and in particular to a multifunctional air purifying device for removing indoor pollution by a thermal decomposition method.

2. Description of Related Art

Indoor environment pollution is becoming more and more serious, and with the continuous improvement of people's living standards, the requirements for indoor health are getting higher and higher, and indoor pollutants are receiving more and more attention. There are many sources of indoor pollutants, such as kitchen fumes, dust on the floor, animal hair in the air, formaldehyde, benzene, xylene, toluene, total volatile organic compound (TVOC) and other harmful gases released from decorative materials, viruses and microorganisms that grow on carpets or wet places. Coupled with the increase in outdoor environmental pollution, and the reduction of natural ventilation, so that a great number of pollutants are continuously deposited. These long-term residual pollutants in the room will seriously affect the indoor environment, endangering human health, and easily cause respiratory diseases, chronic lung diseases, bronchitis, bronchitis and lung cancer.

Cleaners and Indoor air purifiers are commonly used in homes. The cleaners are used to remove dust from the floor, and the air purifiers can be used to purify pollutants in the air. A filter screen is used for treatment of indoor fine particles and bacterial microorganisms, especially the HEPA filter screen, which has a removal rate of more than 99.7% for particles with a particle size of 0.3 µm or more, which is the most effective filter screen media for pollutants such as smoke, dust and bacteria. However, for some newly renovated houses and newly purchased furniture, the release rate of formaldehyde and other gaseous pollutants is slower, the cycle is longer, and the released gas cannot be effectively treated.

Currently, the material for removing harmful gases such as formaldehyde is mainly activated carbon, which is widely used for adsorption purification of benzene, phenols, esters, alcohols, aldehyde organic gases and malodorous gases such as toluene, xylene and benzene. Although this method is simple and feasible, it is easy to achieve saturation, and the activated carbon after adsorption may cause secondary pollution if not treated properly. Photocatalyst is a new method for treating harmful gases. The photocatalyst is applied to the surface of materials. Under the irradiation of ultraviolet light, it not only catalyzes the oxidation reaction with toxic and harmful gases, but also decomposes toxins released by various bacteria or fungi, but the effect at normal temperature is not obvious. Cold catalyst is another new air purification material after photocatalyst. As a new type of catalyst, the cold catalyst can catalyze formaldehyde, ammonia, toluene, xylene, hydrogen sulfide and various harmful gases in TVOC at room temperature to oxygen oxidation reaction to produce non-hazardous substances such as water and carbon dioxide, does not cause secondary pollution, and greatly prolongs the service life of the adsorbent. The cold catalyst is one of the safe and environmentally friendly materials for the future and most suitable for healthy homes.

SUMMARY OF THE INVENTION

In order to solve various problems existing in the current environment, the present invention provides a multifunctional air purifying device for removing indoor pollution by using a thermal decomposition method, the air purifying device further combines with an air treatment unit to allow formaldehyde in a furniture decoration. Volatile gases are volatilized, adsorbed and degraded, and particulates and microorganisms on the floor and in the air are eliminated. A humidifier is further combined to provide a more comfortable and healthy environment while purifying indoor air.

A technology approach is provided as follows in accordance with the present invention: a multifunctional air purifying device for removing indoor pollution by thermal decomposition, includes an air treatment unit, and further includes a air collection heater. The air collection heater and the air treatment unit are connected by a hose. The air collection heater includes an air collection hood, two sterilizing infrared light tubes and two heating ultraviolet light tubes. The two infrared light tubes are symmetrically disposed on both sides of an inlet of the air collection hood, and the two ultraviolet lamps are symmetrically disposed on the other sides of the inlet of the air collection hood. The air treatment unit includes a cylinder wall, a filter screen and an air cap, a top of the cylinder wall is connected to the air cap, an upper inner side of the cylinder wall is provided with an annular water tank, and the filter screen passes through a central hole of the annular water tank and is fixedly connected with the air cap, and a fan is arranged at a joint between the filter screen and the air cap. The filter screen includes an early effect filter screen, a HEPA filter screen, an activated carbon filter screen and a cold catalyst filter screen arranged in that order from a bottom to a top. A humidifier is connected by a pipe to the annular water tank and a nozzle located in the air cap, and the nozzle is located at exhaust ports of the air cap.

The cylinder wall is made of a transparent material in a cylindrical shape, and an air inlet of the hose is disposed in a middle of the cylinder wall, and adopts a structure tangential to the cylinder wall, the exhausting ports are symmetrically disposed on both sides of the air cap, and the bottom of the cylinder wall is provided with a garbage cleaning port.

A seamless fit is adopted between the annular water tank and a structure of the filter screen.

The humidifier is fixed to the inner side of the upper portion of the cylinder wall and corresponds to the two exhaust ports on the air cap.

In accordance with the above technology solutions, the present invention provides a multifunctional air purifying device for removing indoor pollution by thermal decomposition, the air purifying device includes an air treatment unit and a air collection heater. The air collection heater is provided with an infrared lamp tube and an ultraviolet lamp tube, an annular water tank is arranged on an inner side of the upper part of the air treatment unit, and a filter screen runs through the annular water tank to connect with an air cap, with a fan at the connection between the filter screen and the air cap. The filter screen includes an early effect filter screen, a HEPA filter screen, an activated carbon filter screen and a cold catalyst filter screen arranged in that order from a bottom to a top. A humidifier is connected with the annular sink and a nozzle at an exhaust. The purifying device adopts a heating sterilizer, which greatly promotes the volatilization speed of harmful gases in the object and shortens the volatilization period. The four-layer filtration greatly improves the air treatment effect and avoids the occurrence of secondary pollution. The filter screen is layered and arranged for easy cleaning and replacement. The purification device is provided with an air humidifier at the exhaust port, thus the air is cleaned while taking into consideration the comfort requirements.

SUMMARY OF THE DRAWING(S)

Figure 1:
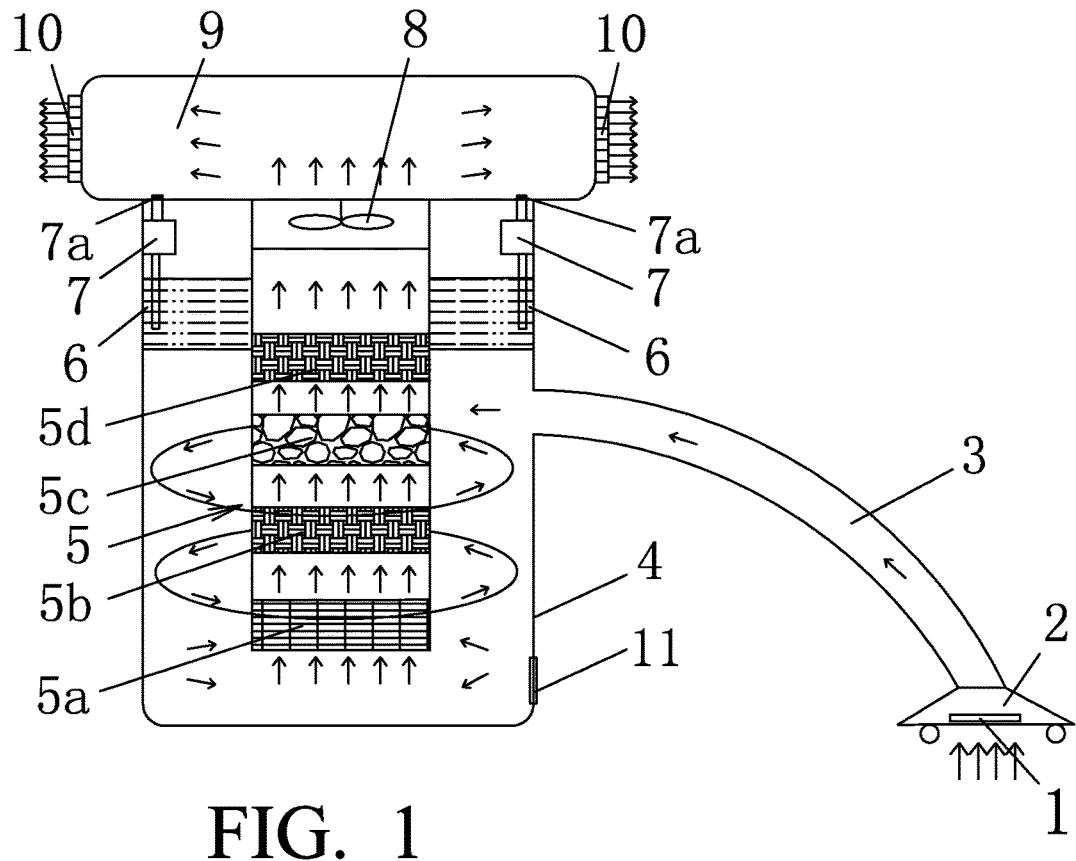
FIG. 1 is a schematic diagram of a multifunctional air purifying device for removing indoor pollution by thermal decomposition according to an embodiment of the present invention.
Figure 2:
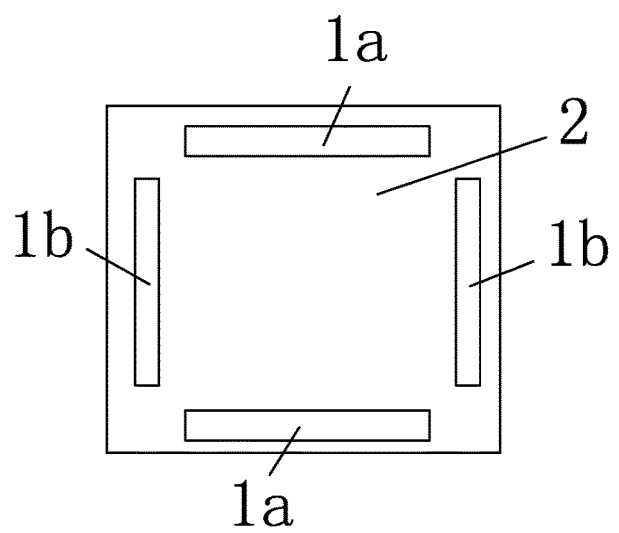
FIG. 2 is a schematic diagram of a air collection heater.

In the FIGS. 1 and 2, 1 represents heating tube; 1a represents infrared light tube; 1b represents ultraviolet lamp; 2 represents air collection hood; 3 represents hose; 4 represents cylinder wall; 5 represents filter screen; 5a represents early effect filter screen; 5b represents HEPA filter screen; 5c represents activated carbon filter screen; 5d represents cold catalyst filter screen; 6 represents annular water tank; 7 represents humidifier; 8 represents fan; 9 represents air cap; 10 represents exhaust port; 11 presents garbage cleaning port.

DETAILED DESCRIPTION OF EMBODIMENTS OF THE PRESENT INVENTION

The invention will be further described in detail with reference to the accompanying drawings.

FIGS. 1 and 2 show a schematic diagram of a multifunctional air purifying apparatus for removing indoor pollution by thermal decomposition. In the Figures, the multifunctional air purifying device for removing indoor pollution by thermal decomposition includes an air treatment unit and a air collection heater, and the air collection heater is connected with the air treatment unit by a hose 3. The air collection heater includes an air collection hood 2, two infrared light tubes 1a for sterilization, and two ultraviolet light tubes 1b for heating. The two infrared light tubes 1a are symmetrically arranged on both sides of the inlet of the air collection hood 2, and the two ultraviolet lamps 1b are symmetrically disposed on the other sides of the inlet of the air collection hood 2. The air treatment unit includes a cylinder wall 4, a filter screen 5 and an air cap 9. A top of the cylinder wall 4 is connected to the air cap 9. The cylinder wall 4 is formed by a transparent material in a cylindrical shape, and an air inlet connected to the hose 3 is arranged in a middle portion of the cylinder wall 4, and the air inlet is in a structure tangential to the cylinder wall 4. Exhaust ports 10 are symmetrically arranged on both sides of the air cap 9, and a bottom of the cylinder wall 4 is provided with a garbage cleaning port 11. An annular water tank 6 is arranged in the inner side of the upper portion of the cylinder wall 4, and the filter screen 5 is fixedly connected to the air cap 9 through a central hole of the annular water tank 6, and a seamless fit is adopted between the annular water tank 6 and the filter screen 5. A fan 8 is provided at a joint between the filter screen 5 and the air cap 9. The filter screen 5 is provided with an early effect filter screen 5a, a high efficiency particulate air (HEPA) filter screen 5b, an activated carbon filter screen 5c, and a cold catalyst filter screen 5d in that order from bottom to top. The humidifier 7 is connected to the annular water tank 6 and a nozzle 7a located in the air cap 9 by means of a pipe, and the nozzle 7a is provided at exhaust ports 10 of the air cap 9. The humidifier 7 is fixed to the inner side of the upper portion of the cylinder wall 4, corresponding to the two exhaust ports 10 on the air cap 9.

With the above technology approach, when the air collection heater uses the infrared lamp tube, the surface of the object can be heated to allow the volatilization of the harmful gas inside the object, and when the ultraviolet lamp is used, not only the decomposition of formaldehyde but also sterilize the surface of the object, and remove microbial contaminants. The harmful gases volatilized and the dust and air near the objects will pass through the air collection hood through the hose into the cylindrical air treatment unit. The air treatment unit is divided into an air layer and a filter layer. The inhaled air is blown obliquely into the cylinder along the wall of the cylinder to form a cyclone. The bottom end of the cylinder contains a small amount of water to accelerate the sedimentation of the particles and objects with large gravity and dissolve in the water. Then the air will pass through the early effect filter screen (except large particles), HEPA filter screen (dust removal, sterilization), activated carbon filter screen (adsorption of harmful gases and odour such as formaldehyde) and cold catalyst filter screen (decomposed formaldehyde, benzene, xylene, toluene, TVOC and other harmful gases) from bottom to top, then it is humidified and discharged into the room.

There are two layers of filter screens for removing harmful gases: activated carbon filter screens and cold catalyst filter screens. Considering that the concentration of harmful gases in the air is high, the adsorption effect of the activated carbon filter screen cannot meet the requirements of air quality, so that a cold catalyst filter screen is added. That is to avoid the occurrence of secondary pollution, and improve the purification effect. It will undergo a catalytic reaction under normal temperature conditions, from simple physical adsorption to chemical adsorption, decomposing toxic and odorous harmful gases into harmless and odourless water and carbon dioxide, and the cold catalyst after the reaction does not change, and has long-term function, greatly extending the service life of the adsorbent material.

The humidifier automatically monitors the relative humidity in the environment. When the indoor air is dry, the humidification switch is automatically turned on, and the humidification function switch is set at the exhaust port, and the air purified from the water tank to the air cap is sprayed with water vapor, thereby achieving the purpose of humidification, and avoiding contamination of the filter screen by moisture and corrosion to the fan. When the indoor air is wet, the humidification function is turned off. The sink is made of transparent material to observe the water level and water quality.

There are two infrared tubes and two UV tubes in the air collection hood. The UV lamp can be used to sterilize the surface of the object and decompose some harmful gases. Infrared lamps can be used to heat the surface of objects and promote the volatilization of harmful gases inside. The bottom of the air collection hood is equipped with rolling pulleys, which saves time and effort. Harmful gases volatilized on the surface of the object, dust from the floor, and indoor air can be transported to the air purifying device through the air collection hood and hose. The airflow is tangentially blown into the inner side of the cylinder wall through the air inlet, causing the airflow to spirally move, and larger objects and particulate matter are deposited and dissolved in the bottom water. The airflow then passes through the filter screen for layer-by-layer filtration. The first through the early effect filter screen at the bottom, it mainly filters out the hair, fiber fluff, large particles, dander, etc. in the indoor floor and air; then passes through the HEPA filter screen, for effectively removing inhalable particles, cigarette smoke, pollen and bacteria in the air. Subsequently, the air passes through the activated carbon filter screen, which has high adsorption performance, and can be used to remove volatile organic compounds such as formaldehyde, toluene, hydrogen sulfide, chlorobenzene and air pollutants, and also deodorize and remove odour, which has good purification effect. Finally, through the cold catalyst filter screen, where dissociative formaldehyde, ammonia, TVOC, hydrogen sulfide and other harmful gases in the residual air react with oxygen to form water and carbon dioxide. Considering that when the concentration of harmful gases in the gas stream is high, only the activated carbon filter screen alone cannot meet the air quality requirements, so that the two-layer filtration including the activated carbon filter screen and the cold catalyst filter screen is adopted.

The air passes through a roasting effect in the air collection hood, the water vapor content is lowered, the air is relatively dry, and the requirements for human comfort are not satisfied. The treated air is subjected to humidification, and pure water is added to the annular water tank, and the moisture is sprayed into the air cap through the humidifier, and the amount of humidifier sprayed can be automaticly adjusted by the relative humidity in the indoor air. The filtered and humidified air is discharged into the room through the exhaust port, and the air is continuously circulated to continuously purify the indoor air.

The embodiments of present invention are the same as the best mode of the present invention described above.

In industrial applicability, when the gas gathering heater uses the infrared lamp tube, the surface of the object can be heated to allow the volatilization of the harmful gas inside the object, and when the ultraviolet lamp is used, not only the decomposition of formaldehyde but also sterilize the surface of the object, and remove microbial contaminants. The harmful gases volatilized and the dust and air near the objects will pass through the gas gathering hood through the hose into the cylindrical air treatment unit. The air treatment unit is divided into an air layer and a filter layer. The inhaled air is blown obliquely into the cylinder along the wall of the cylinder to form a cyclone. The bottom end of the cylinder contains a small amount of water to accelerate the sedimentation of the particles and objects with large gravity and dissolve in the water. Then the air will pass through the early effect filter (except large particles), HEPA filter (dust removal, sterilization), activated carbon filter (adsorption of harmful gases and odour such as formaldehyde) and cold catalyst filter (decomposed formaldehyde, benzene, xylene, toluene, TVOC and other harmful gases) from bottom to top, then it is humidified and discharged into the room.

What is claimed is:

1. A multifunctional air purifying device for removing indoor pollution by thermal decomposition, comprising an air treatment unit,
    wherein the air purifying device further comprises an air collection heater, and the air collection heater and the air treatment unit are connected by a hose (3), the air collection heater comprises an air collection hood (2), two sterilizing infrared light tubes (1a) and two heating ultraviolet light tubes (1b), the two infrared light tubes (1a) are symmetrically disposed on both sides of an inlet of the air collection hood (2), and the two ultraviolet lamps (1b) are symmetrically disposed on the other sides of the inlet of the air collection hood (2);
    wherein the air treatment unit comprises a cylinder wall (4), a filter screen (5) and an air cap (9), the top of the cylinder wall (4) is connected to the air cap (9), the upper inner side of the cylinder wall (4) is provided with an annular water tank (6), and the filter screen (5) runs through a central hole of the annular water tank (6) and is fixedly connected with the air cap (9), and a fan (8) is arranged at a joint between the filter screen (5) and the air cap (9); the filter screen (5) comprises an early effect filter screen (5a) and a HEPA filter screen (5b), an activated carbon filter screen (5c) and a cold catalyst filter screen (5d) arranged in that order from a bottom to a top; a humidifier (7) is connected to the annular water tank (6) and a nozzle (7a) located in the air cap (9) by a pipe, the nozzle (7a) being located at exhaust ports (10) of the air cap (9).

2. The air purifying device according to claim 1, wherein the cylinder wall (4) is made of a transparent material in a cylindrical shape, and an air inlet of the hose (3) is disposed in a middle of the cylinder wall (4), and adopts a structure tangential to the cylinder wall (4), the exhausting port (10) are symmetrically disposed on both sides of the air cap (9), and the bottom of the cylinder wall (4) is provided with a garbage cleaning port (11).

3. The air purifying device according to claim 1, wherein a seamless fit is adopted between the annular water tank (6) and a structure of the filter screen (5).

4. The air purifying device according to claim 1, wherein the humidifier (7) is fixed to the inner side of the upper portion of the cylinder wall (4) and corresponds to the two exhaust ports (10) on the air cap (9).

* * * * *